United States Patent [19]

Demisch

[11] Patent Number: 5,050,434

[45] Date of Patent: Sep. 24, 1991

[54] CAPACITIVE HUMIDITY SENSOR

[75] Inventor: Ullrich Demisch, Freiburg i.Br., Fed. Rep. of Germany

[73] Assignee: Testoterm Messtechnik GmbH & Co., Lenzkirch, Fed. Rep. of Germany

[21] Appl. No.: 536,882

[22] Filed: Jun. 13, 1990

[30] Foreign Application Priority Data

Jun. 19, 1989 [DE] Fed. Rep. of Germany ....... 3919864

[51] Int. Cl.$^5$ .............................................. G01W 1/00
[52] U.S. Cl. .................................. 73/336.5; 73/29.05; 361/286
[58] Field of Search ............................ 73/336.5, 29.05; 338/35; 361/323, 286

[56] References Cited

U.S. PATENT DOCUMENTS

| | | | |
|---|---|---|---|
| 4,564,882 | 1/1986 | Baxter et al. | 73/336.5 X |
| 4,672,506 | 6/1987 | Deguchi et al. | 361/323 |
| 4,761,710 | 8/1988 | Chen | 361/286 |
| 4,920,451 | 4/1990 | Sakai et al. | 361/286 |
| 4,965,698 | 10/1990 | Thoma et al. | 361/286 |

FOREIGN PATENT DOCUMENTS

| | | |
|---|---|---|
| 2848034 | 11/1978 | Fed. Rep. of Germany . |
| 3339276 | 10/1983 | Fed. Rep. of Germany . |
| 2149922 | 6/1985 | United Kingdom ................ 361/286 |

OTHER PUBLICATIONS

"Dunnschicht-Feuchtesensoren" by Von Dr. U. Demisch, Messen Prufen Automatisieren, Sep. 1989.

"Marktubersicht: Dunnschicht-Feuchtesensoren" by U. Demisch Elektronisches Messen Physikalischer und Chemischer Werte Sensor Magazine, No. 3 vol. Sep. 5, 1989.

Primary Examiner—Hezron E. Williams
Assistant Examiner—Joseph W. Roskos
Attorney, Agent, or Firm—Mason, Fenwick & Lawrence

[57] ABSTRACT

A capacitive humidity sensor includes a capacitor with two metallic electrodes 12, 15, with electrode 15 formed of a moisture-permeable metallic layer. A moisture-sensitive polymer film 14 situated between the electrodes serves as a dielectric. The film 14 is advantageously chosen to be polyether imide.

8 Claims, 4 Drawing Sheets

CAPACITIVE HUMIDITY SENSOR

BACKGROUND OF THE INVENTION

The invention relates to a capacitive humidity sensor.

A humidity sensor of this kind is a capacitor with at least two electrodes, between which a humidity-sensitive dielectric is located. At least one of the two electrodes, which can consist of a differently shaped metallic layer, is provided on an electrically highly insulating support which preferably consists of glass or ceramic and is frequently referred to as a substrate. The second electrode, outwardly located and likewise designed as a metallic layer, is permeable to moisture, especially to water vapor, i.e. the water molecules in the air can diffuse through it.

Between these two electrode layers is the humidity-sensitive dieletric, critical for humidity measurement.

In previously known humidity sensors of this kind, a polymer film is used as the dielectric layer.

The company known as Vaisala Oy, Helsinki, offers under the name of "Humicap" a thin-layer sensor in which a humidity-sensitive polymer of the cellulose acetate type is mounted on a glass substrate as a carrier for two-layer gold electrodes. In this arrangement, the second electrode is formed by a very thin gold electrode 100 to 200 angstroms thick, serving as a common reference electrode for the two electrodes mounted on the glass substrate. These two lower electrodes are contacted, so that the capacitance between the two lower electrodes is measured with the polymer dielectric, with the dielectric field lines running parallel to one another to the upper, zero-potential electrode.

In another humidity sensor made by the Coreci Company and designated "H 2000", a polymer is again used as the dielectric and consists of cellulose acetate butyrate. The lower electrode is made of tantalum sputtered onto a glass substrate, said tantalum then being oxidized. The outwardly located humidity-permeable electrode consists of a 1 micron-thick chromium layer, which is contacted by a chromium-nickel-gold electrode. To decrease the response time, this sensor arrangement is subjected after manufacture to a heat treatment such that the chrome electrodes, together with the polymer layer below them, are fractured to form trenches.

German 3,339,276 A1 teaches a similar capacitive humidity sensor, in which a polyimide is used as the humidity-sensitive layer. Comb-shaped gold electrodes are mounted on this dielectric layer, said electrodes being staggered with respect to the tantalum electrodes likewise arranged combwise on the glass substrate. This arrangement has the advantage that the water molecules can penetrate directly and hence very rapidly into the humidity-sensitive layer.

Use of a polyimide foil for a capacitive humidity sensor is also known from DE 28 48 034 A1. This humidity sensor has two metallic layers forming the electrodes, one of which is a thin gold layer permeable to water vapor while the other is made of a non-rusting iron-chromium-nickel steel.

The change in capacitance of a humidity sensor of this kind in the presence of air with different moisture content is based on the fact that the water molecules in the air diffuse into the polymer film forming the dielectric, changing the dielectric constant (DC) and thus the capacitance of the resultant capacitor. While the dielectric constant of polymers is between 2 and 3, the dielectric constant of water is 80. This means that when water molecules penetrate the dielectric layer, the capacitance of a capacitor that can be used to measure humidity, increases.

It is also important for measurement results to be both reproducible and largely independent of other physical or chemical factors.

The following properties are important for selecting the polymer layer for the dielectric:

1. Reproducible dependence of the capacitance on relative humidity (RH).
2. Ideally no drifting, especially at high humidity levels. Previously known humidity sensors using polymer dielectrics do not yet meet this condition satisfactorily.
3. Ability to withstand high temperatures.
   The majority of sensors known thus far can be used only at temperatures up to 80° C.
4. Usability over the entire humidity range from 0 to 100% RH.
   Use of previously known humidity sensors at humidities above 90% RH is only possible for short periods of time as a rule, since in this range the electrical characteristics of the humidity sensor are no longer reproducible, in other words the capacitance of the sensors shows pronounced drifting.
5. High resistance to foreign gases such as $SO_2$, $C_xH_y$, $NH_3$, etc.

The dielectrics used heretofore, especially polymers from the polyimide group, show pronounced drifting and a lack of reproducibility as regards electric characteristics when used in humidity sensors at humidity levels about 90% RH.

SUMMARY OF THE INVENTION

The goal of the present invention is to find a dielectric for the above humidity sensor which largely meets the above-mentioned conditions.

To achieve this goal, according to the present invention a polymer film of polyether imide is proposed as the dielectric.

This polymer, used heretofore because of its good flow properties to make injection-molded parts for aircraft and motor vehicles, for electrical devices and domestic appliances, and for membranes that separate gases (U.S. Pat. No. 4,156,597), surprisingly achieves the stated goal in the capacitive humidity sensor of the above type and meets the above-mentioned conditions better than all of the dielectrics mentioned heretofore.

The further design of the humidity sensor is the subject of the subclaims.

BRIEF DESCRIPTION OF THE DRAWINGS

The subject of the invention will now be described with reference to an embodiment and on the basis of measurement results and their curves. In the drawings described below.

DETAILED DESCRIPTION OF THE PREFERRED EMBODIMENTS

Figure 1:
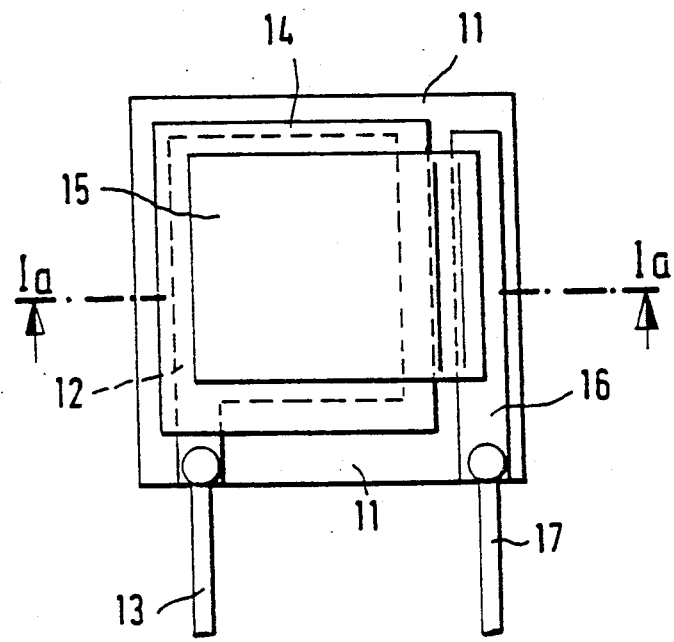
FIG. 1 is a top view of a humidity sensor according to the invention in an enlarged representation.
Figure 1A:
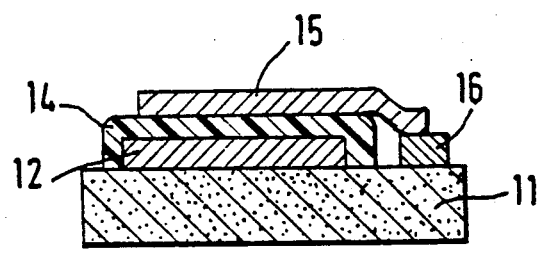
FIG. 1a is a section along line Ia—Ia in FIG. 1.

FIGS. 1 and 1a show one possible embodiment of the humidity sensor according to the invention. The substrate 11 that carries the sensor consists of an electrically highly insultating material, made of glass or ceramic in the embodiment. A metallic layer 12 is mounted on this substrate as a first electrode, said layer being made of tantalum, tantalum/tantalum oxide, or gold, connected elecrically with a lead 13. This layer is covered by a polymer film 14 forming the dielectric, said film being made of polyether imide according to the present invention. This polymer film 14 can be formed both by a self-supporting foil film and also by a polymer layer applied in the liquid state.

The sensor arrangement is covered on the top by a second electrode, cover electrode 15, made of a metal permeable to water vapor, preferably gold. This cover electrode is preferably applied by evaporation onto the polymer film.

This electrode 15 is connected in an electrically conducting manner with a connecting electrode 16, which, like electrode 15, is electrically insulated from the one provided on substrate 11 and made of tantalum or gold. The power supply to this electrode 16 is through wire lead 17.

Figure 2:
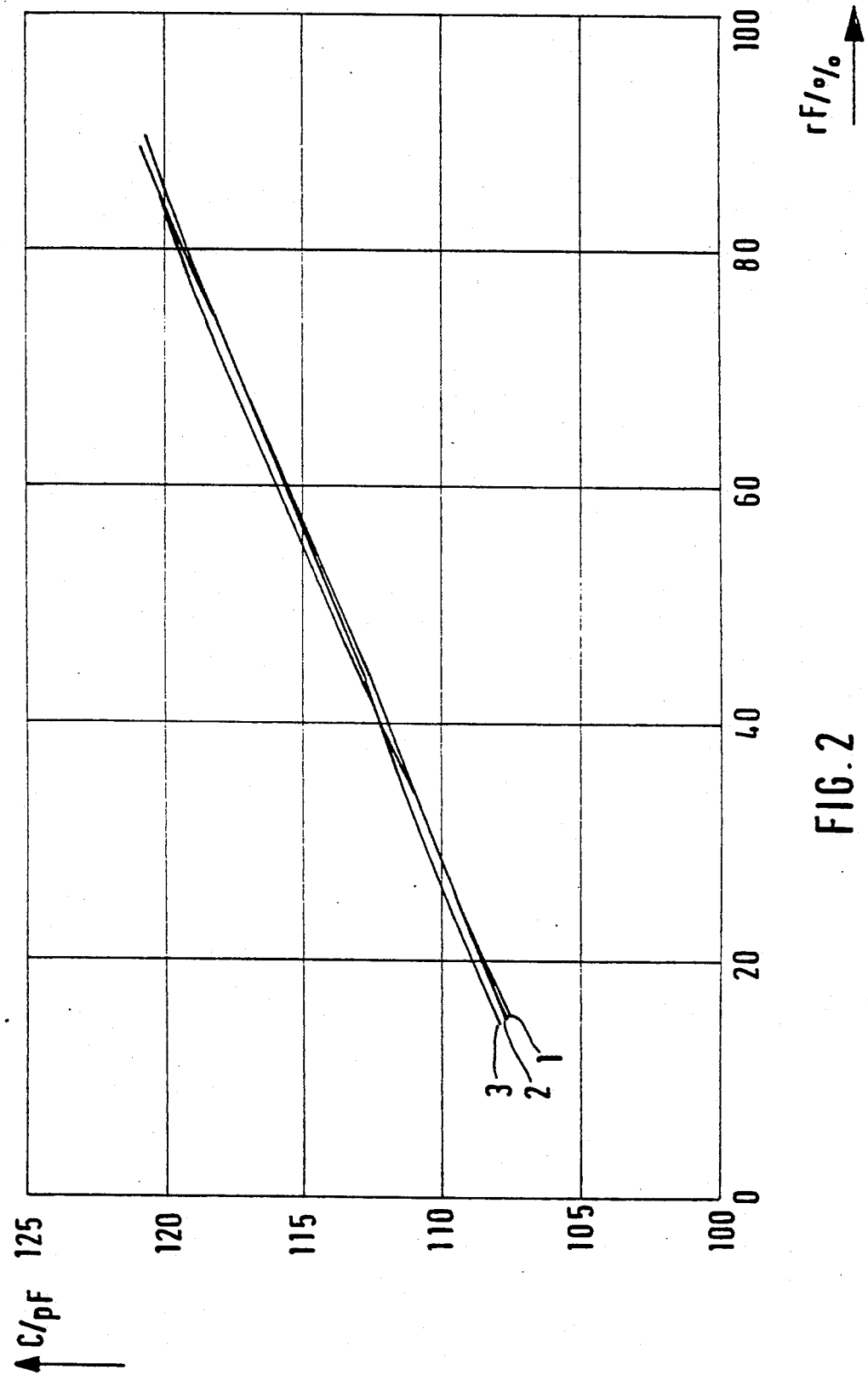
FIG. 2 is a graph showing capacitance as a function of relative humidity.

In a series of measurements performed over a measurement range of 15% to 90% relative humidity, a largely linear relationship to capacitance was found; the latter, in the measuring system, is between 107 and 120 pF. This indicates a sensitivity of approximately 0.175 pF per percent RH. Suprisingly, the curves in FIG. 2 exhibit very low hysteresis. According to FIG. 1, the sensor is exposed to relative humidity variable between 15% and 90% at 25° C. After storing the sensor for about 6 hours at 50° C. and 50% relative humidity, the sensor according to curve 2 again is exposed to a variable humidity of 15% to 90% and then, as shown in curve 3, to one of 90% to 15%.

Not only is the low hysteresis surprising, but so is the outstanding reproducibility of the 25° C. curve. The 325° C. curves 1, 2, and 3 show only a maximum deviation of 0.25 pF from one another, corresponding to a humidity fluctuation of 1.5% RH.

Figure 3:
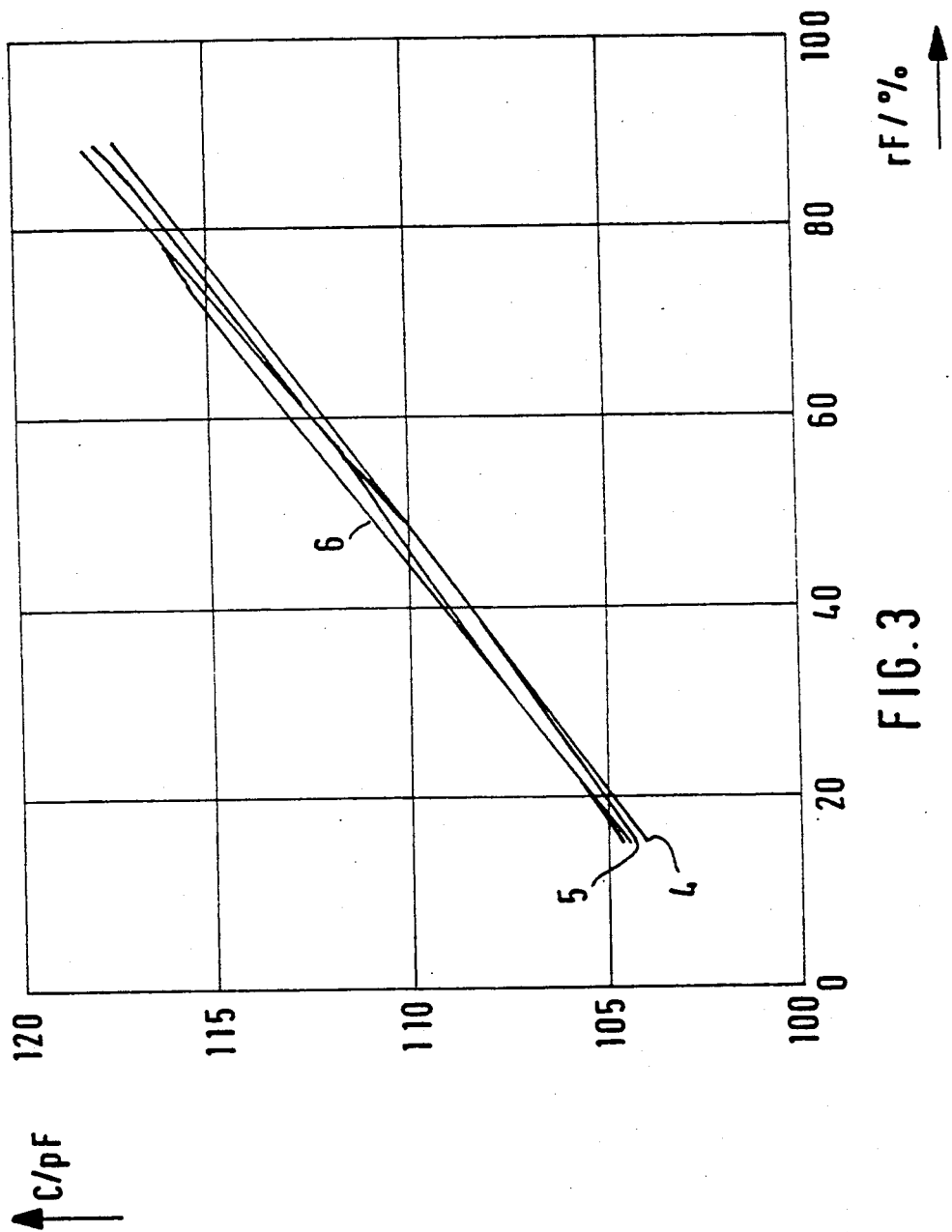
FIG. 3 is a graph showing capacitance as a function of relative humidity before and after storage in a "weather house.

This outstanding reproducibility is also proven by measurements conducted under practical conditions, as shown in the graph in FIG. 3.

This indicates that the humidity sensor was first exposed to a variable humidity of 15% to 90% at 25° C. (curve 4).

After being stored for two weeks in the open-air "weather house," during which time the sensor was exposed to the daytime and nighttime rhythms of temperature, humidity and solor radiation, the sensor was again subjected to the change in humidity described above in curve 5.

Then the hysteresis curve according to curve 6 was recorded.

As the curves indicate, the reproducibility of the capacitance lies in a range of ±0.25 pF which corresponds to a range of fluctuation in humidity of only ±1.5%.

Figure 4:
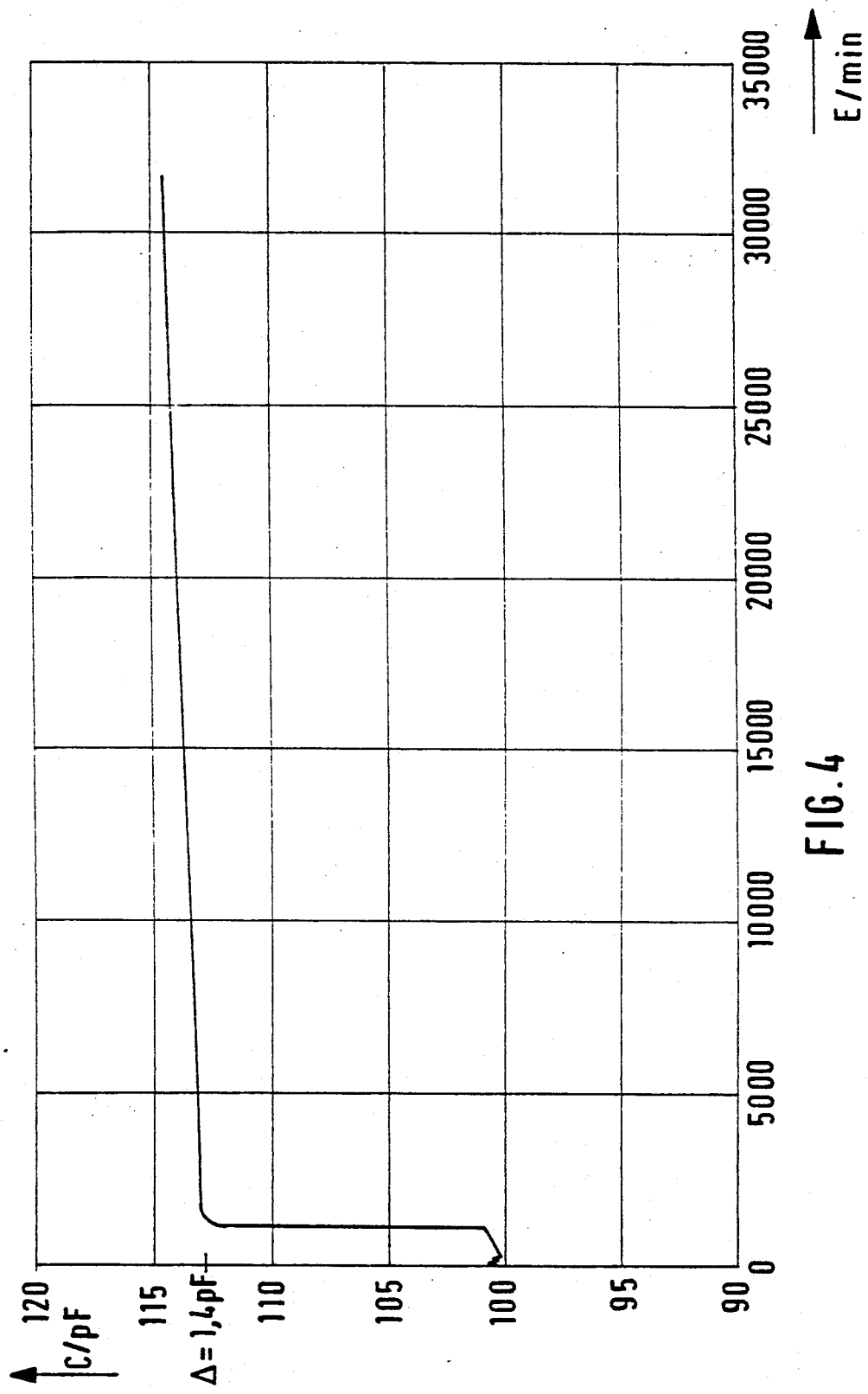
" and FIG. 4 is a graph showing capacitance over a period of 35,000 minutes (approximately 21 days).

As the curve in FIG. 4 shows, the humidity sensor according to the invention also exhibits outstanding long-term behavior in the high humidity range. Over a measurement time of 21 days (about 35,000 minutes), the capacitance remained nearly constant at about 113 pF.

The measurement results show that the drift of the capacitance is only 1.4 pF, corresponding to a humidity drift of 9%.

I claim:

1. A capacitive humidity sensor, comprising:
   a) a capacitor with at least two metallic layers forming electrodes, at least one of which is permeable to water vapor; and
   b) a humidity-sensitive polyimide film disposed between the electrodes as a dielectric, the polyimide film consisting of polyether imide.

2. The capacitive humidity sensor of claim 1, further comprising:
   a substrate having high electrical insulation properties, on which is disposed a said metallic layer.

3. The capacitive humidity sensor of claim 1, wherein one of the electrodes is selected from the group consisting of tantalum, tantalum/tantalum oxide, gold, gold/nickel, or silver/palladium; and another of the electrodes is of gold and is water permeable.

4. The capacitive humidity sensor of claim 3, further comprising a substrate of glass or ceramic, a said electrode being on said substrate.

5. The capacitive humidity sensor of claim 1, wherein:
   a first said electrode is provided on a substrate and includes tantalum or tantalum/tantalum oxide;
   the polyether imide film completely covers the first electrode, the film having a side which is engaged by a second electrode;
   the second electrode is of gold and is water-vapor permeable and has a laterally projecting edge; and
   a third electrode is provided on the substrate electrically insulated from the first said electrode, includes tantalum or tantalum/tantalum oxide, and contacts the laterally projecting edge of the second electrode.

6. The capacitive humidity sensor of claim 1, wherein the polyimide film is set from liquid polyether imide.

7. The capacitive humidity sensor of claim 1, wherein the polyether imide film is a self-supporting foil film.

8. The capacitive humidity sensor of claim 1, wherein at least one electrode is evaporated onto the polyether imide film.

* * * * *